US009566309B2

(12) United States Patent
Bombardelli et al.

(10) Patent No.: US 9,566,309 B2
(45) Date of Patent: Feb. 14, 2017

(54) COMPOSITIONS FOR TREATMENT OF CANCER-RELATED FATIGUE

(71) Applicant: INDENA S.P.A., Milan (IT)

(72) Inventors: Ezio Bombardelli, Gropello Cairoli (IT); Fabrizio Corti, Milan (IT)

(73) Assignee: INDENA S.P.A., Milan (IT)

( * ) Notice: Subject to any disclaimer, the term of this patent is extended or adjusted under 35 U.S.C. 154(b) by 67 days.

(21) Appl. No.: 14/416,346

(22) PCT Filed: Jul. 11, 2013

(86) PCT No.: PCT/EP2013/064711
§ 371 (c)(1),
(2) Date: Jan. 22, 2015

(87) PCT Pub. No.: WO2014/016137
PCT Pub. Date: Jan. 30, 2014

(65) Prior Publication Data

US 2015/0202246 A1 Jul. 23, 2015

(30) Foreign Application Priority Data

Jul. 27, 2012 (IT) .......................... M12012A001317

(51) Int. Cl.

| | |
|---|---|
| ***A61K 36/254*** | (2006.01) |
| ***A61K 36/906*** | (2006.01) |
| ***A61K 36/28*** | (2006.01) |
| ***A61K 36/9068*** | (2006.01) |
| ***A61K 36/258*** | (2006.01) |
| ***A61K 31/685*** | (2006.01) |

(52) U.S. Cl.
CPC ......... *A61K 36/9068* (2013.01); *A61K 31/685* (2013.01); *A61K 36/258* (2013.01); *A61K 36/28* (2013.01)

(58) Field of Classification Search
CPC ............................ A61K 36/258; A61K 36/906
See application file for complete search history.

(56) References Cited

U.S. PATENT DOCUMENTS

| | | | | |
|---|---|---|---|---|
| 7,384,919 | B2 * | 6/2008 | Benesova et al. | 514/22 |
| 2003/0206978 | A1 * | 11/2003 | Sherwood et al. | 424/728 |
| 2005/0002962 | A1 * | 1/2005 | Pasco et al. | 424/195.15 |
| 2005/0031710 | A1 | 2/2005 | D'Adamo | |

FOREIGN PATENT DOCUMENTS

| | | |
|---|---|---|
| WO | 2004093518 | 11/2004 |
| WO | 2010083967 | 7/2010 |
| WO | WO 2010083967 A1 * | 7/2010 |
| WO | 2012013551 | 2/2012 |

OTHER PUBLICATIONS

Search and Written Opinion of counterpart PCT/EP2013/064711 of Sep. 2, 2013.
International Preliminary Report on Patentability of counterpart PCT/EP2013/064711 of Jul. 16, 2014.

* cited by examiner

*Primary Examiner* — Chris R Tate
*Assistant Examiner* — Russell Fiebig
(74) *Attorney, Agent, or Firm* — Silvia Salvadori, P.C.; Silvia Salvadori

(57) ABSTRACT

Disclosed are compositions containing extracts of (a) *Panax ginseng* C. A. Mayer, (b) *Zingiber officinale*, (c) *Echinacea angustifolia* and (d) *Silybum marianum* or the phospholipid complex of silybin with phospholipids as active ingredients, mixed with suitable excipients.

5 Claims, No Drawings

COMPOSITIONS FOR TREATMENT OF CANCER-RELATED FATIGUE

This application is a U.S. national stage of PCT/EP2013/064711 filed on 11 Jul. 2013, which claims priority to and the benefit of Italian Application No. MI2012A001317 filed on 27 Jul. 2012, the contents of which are incorporated herein by reference in their entireties.

The present invention relates to formulations containing a combination of extracts of *Panax ginseng* C. A. Mayer, *Zingiber officinale, Echinacea angustifolia* and *Silybum marianum*. The compositions according to the invention are useful for the treatment of fatigue in cancer patients.

PRIOR ART

The availability of effective cancer treatments has led to a significant increase in the number of "long-term survivors", highlighting the basic problem of guaranteeing an increasingly high quality of life for these patients. Cancer-related fatigue, which prejudices the quality of the life to a crucial extent in psychosocial terms, is a generalised symptom that is difficult to define. Although its origin is multifactorial and physiologically based, its perception remains individual, and associated with a complex psychological picture. It is basically characterised as weakness, namely reduced ability to exert the maximum muscle strength, and tiring easily, i.e. inability to maintain an activity for a long time. Some researchers attempt to identify the source of fatigue as a state of muscle weakness, while others consider it mainly from the behavioural standpoint as a generalised state of malaise. Cancer-related fatigue is a severe symptom that affects between 28 and 90% of cancer patients and between 80 and 90% of those treated with chemo- and radiotherapy, and can prejudice the quality of the life for long periods. even after the treatments are discontinued [*CA: Cancer J. Cli.,* 2012, 62 (1), 10-29]. Cancer-related fatigue is very different from the usual fatigue caused by effort or stress, from which the patient recovers with rest. More than 75% of cancer patients report being overtired, with very severe general weakness requiring unusual rest, which is often not restorative. A very large proportion of patients also report lack of motivation, anxiety, respiratory problems, exhaustion with cognitive disorders and lack of sleep. This syndrome is often accompanied by diffuse pain, reducing the patient's compliance during maintenance treatments, and above all the recovery of those still of working age. Chemotherapy and radiotherapy, which are essential weapons against cancer, induce a series of adverse events such as generalised inflammation, hepatotoxicity, nephrotoxicity, and neurological damage, which involve a severe state of debilitation. Moreover, the damage to the immune system commonly observed in cancer treatment produces immunosuppression symptoms that make the patient vulnerable to attack by infectious agents. Radiation treatment also leads to anaemia, weight loss, anorexia, nausea and peripheral neuropathy.

This complex clinical picture adversely affects the quality of the patient's life. Various attempts have been made to improve the symptoms, but with little success.

The palliative treatments currently used include Cox-2 inhibitors, methylphenidate to improve the attention span and alertness, steroids and glucocorticoids; these medicaments have major side effects, with a sometimes highly critical risk-benefit ratio, and above all are difficult to use in combination.

Pharmacological treatments with substances of natural origin, such as medicinal plant extracts, have also been proposed.

One example is *ginseng* extracts which, together with a well-known anti-fatigue and energising action, have immunostimulating and anticancer properties. One study [*Proc. Am. Soc. Clin. Oncol.* 2003 *Abst.* 2947] has given encouraging results, with a significant improvement in fatigue compared with the placebo group. However, in other studies, the results were erratic or doubtful, and sometimes unfavourable, perhaps because the preparations were not standardised.

Silybin, present in *Silybum marianum* extract, has exhibited an effective cytoprotective action against cytotoxic substances and support for the liver functions in various pathophysiological conditions, in experimental animal models and human clinical trials. Complexing with phospholipids aids its absorption, even under conditions of altered gastrointestinal functionality. In the specific field of palliative care for cancer patients, a recent study on young people who underwent the typical treatment for acute lymphoblastic leukaemia exhibited high safety levels and a favourable reduction in liver toxicity indexes [*Cancer,* 2010, 116, 506-13.]

*Zingiber officinale*, due to the anti-inflammatory action of gingerols and their congeners, acts by mitigating the inflammatory state correlated with the release of proinflammatory cytokines, thus improving the patient's quality of life. Moreover, due to its well-known anti-nausea action, it has already been indicated by numerous studies as an effective remedy for the anticipatory nausea that frequently appears in cancer patients, even in the absence of emetogenic substances (chemotherapy drugs) [*Support Care Cancer,* 2012, 20 (7), 1479-89].

*Echinacea* extracts, which have immunostimulating properties, improve the immunosuppression picture, preventing flare-ups of infectious processes and attack by saprophytes which can seriously affect the patient's well-being and quality of life [*Int Immunol. Pharmacol.* 9, 850-85, 2009]. Moreover, *Echinacea angustifolia* alkylamides have an anti-inflammatory and analgesic action comparable with those of known steroidal and non-steroidal anti-inflammatory drugs, with the advantages of faster absorption, not affecting the arachidonic acid cascade, with the consequent gastric damage, and arriving in sufficient quantities at the brain where, interacting with the cannabinoid receptors, they modulate both the painkilling and the symptomatic response.

DESCRIPTION OF THE INVENTION

It has now been found that the combination of *Panax ginseng* C. A. Mayer, *Zingiber officinale, Echinacea angustifolia* and *Silybum marianum* extracts favourably influences the nosological picture, with synergic effects compared with the individual extracts.

The invention therefore provides compositions containing *Panax ginseng* C. A. Mayer, *Zingiber officinale, Echinacea angustifolia* and *Silybum marianum* extracts as active ingredients, admixed with suitable excipients.

The active ingredients according to the invention are known, commercially available or can be prepared by known methods.

The *ginseng* extract is preferably obtained from roots at least four years old, by extraction with water and ethanol mixtures. The extract obtained has a ginsenoside content of 8%, with a ginsenoside Rg1/ginsenoside Rb1 ratio of 0.5/1.

The *Zingiber officinale* extract is preferably a lipophilic extract prepared by extraction from the roots and rhizomes of the plant with carbon dioxide under supercritical conditions, extracting the powder from the root at pressures between 230 and 260 bars in the extractor, preferably 235 bars, at a temperature ranging from 40 to 60° C., preferably 50° C., for a time ranging from 1 to 10 hours, preferably seven hours; the extract is collected in the condenser and dehydrated in inert gas dissolved in n-hexane or heptane, and concentrated under vacuum at a temperature not exceeding 40° C. Said extract contains approx. 30% gingerols, and can be used directly in the formulations according to the present invention.

The *Echinacea angustifolia* extracts can be obtained as disclosed in EP 464298, using supercritical carbon dioxide. The isobutylamide content of said lipophilic extract exceeds 20% by weight.

Although a commercial extract of *Silybum marianum* or its main component, silymarin (a mixture of silybin, silydianin and silychristin) can be employed, the use of the silybin complex with phospholipids, in particular soya lecithins or phosphatidylcholine, obtained as described in EP 209038, is preferred.

The doses of the active ingredients in each form of administration will fall approximately into the ranges specified below:

*Ginseng*: extract 10 to 500 mg, preferably 50 to 250 mg;
*Zingiber officinale*: extract 5 to 100 mg, preferably 10 to 50 mg;
*Echinacea*: extract 1 to 50 mg, preferably 5 to 20 mg;
silybin complex with phospholipid: 10 to 500 mg, preferably 50 to 250 mg.

These doses will preferably be administered orally one to four times a day, preferably three times a day.

The compositions according to the invention will be formulated according to conventional methods, such as those described in "Remington's Pharmaceutical Handbook", Mack Publishing Co., N.Y., USA. In particular, the compositions according to the invention will be formulated according to conventional plant ingredient formulation techniques, which require particular care to be taken to avoid interactions with the excipients and the capsule matrices. Examples of oral formulations are tablets, sugar-coated pills, soft and hard gelatin capsules, and cellulose capsules.

According to a further aspect, the compositions according to the invention can be administered in combination with other substances having useful or complementary activity, predisposing the patient to better resistance to future treatments and fewer relapses.

The examples set out below further illustrate the invention.

Example 1

| Unit composition (film-coated tablet) | |
|---|---|
| Ginseng extract | 100.0 mg |
| Silybin complex with phospholipids | 100.0 mg |
| Ginger extract | 20.0 mg |
| Echinacea extract | 5.0 mg |
| Dicalcium phosphate | 115.0 mg |
| Microcrystalline cellulose | 95.0 mg |
| Croscarmellose sodium | 13.5 mg |
| Silicon dioxide | 4.5 mg |
| Magnesium stearate | 2.0 mg |
| Hydroxypropyl methylcellulose | 10.0 mg |
| Talc | 3.5 mg |
| Titanium dioxide | 1.5 mg≤ |

Example 2

Clinical Trial

To investigate the efficacy of the combination, adult patients with a history of cancer-related fatigue were selected. The ESAS (Edmonton Symptoms Assessment Scale) a tool validated for assessing symptoms in palliative care, was used to evaluate the primary endpoints. The ESAS scale evaluates nine different symptoms, scoring the parameters from 0 to 10, where 0 represents absence of the symptom and 10 represents the symptom in its worst form. A tenth parameter (quality of life), deriving from the average score of the nine indicators used, was also added.

When the patients were selected, the first inclusion criterion was the presence of fatigue for at least one month, and a life expectancy of at least 8 months.

A combination consisting of:

100 mg of *Ginseng* extract having a ginsenoside content of 8% with a ginsenoside Rg1/ginsenoside Rb1 ratio of 0.5/1, prepared by water-ethanol extraction from main roots at least 4 years old, 20 mg of lipophilic extract of *Zingiber officinale* (ginger) having a gingerol and shogaol content of 25%, 5 mg of a lipophilic extract of *Echinacea angustifolia* with a 25% isobutylamide content, 100 mg of silybin complex with phospholipids (phosphatidylcholine 30%) in the ratio of 1 to 2, was administered to male patients who had undergone prior radiotherapy and chemotherapy treatment with primary tumours of the lung, prostate, pancreas and colon for 60 days, with administration three times a day of two tablets taken 30 minutes before meals (breakfast, lunch and evening meal). The extracts were formulated as 470 mg tablets.

The patients were divided into 5 groups, and treated as follows:

Group 1: treated with placebo (excipients of the composition described in example 1);

Group 2: treated with the composition described in example 1;

Group 3: treated with the ginger/*Echinacea* composition (same doses as reported in example 1);

Group 4: treated with silybin phospholipid complex only (same dose as reported in example 1);

Group 5: treated with *Ginseng* extract (same dose as reported in example 1).

The results of the trial are set out in the table below.

| Symptom | Placebo | Composition described in example 1 | *Zingiber*/ Echinacea | Silybin-phospholipid complex | Ginseng extract |
|---|---|---|---|---|---|
| Pain | 7.1 | 2.2 | 6.1 | 6.5 | 7.0 |
| Asthenia | 7.8 | 2.5 | 7.5 | 7.8 | 4.1 |
| Nausea | 8.6 | 1.8 | 4.6 | 6.8 | 6.5 |
| Depression | 6.8 | 2.1 | 6.5 | 6.5 | 5.5 |
| Anxiety | 6.8 | 3.1 | 6.9 | 6.8 | 5.5 |
| Drowsiness | 7.8 | 2.8 | 4.5 | 5.9 | 5.1 |
| Lack of | 8.1 | 3.0 | 6.8 | 6.5 | 6.8 |

-continued

| Symptom | Pla-cebo | Composition described in example 1 | *Zingiber*/ Echinacea | Silybin-phospholipid complex | Ginseng extract |
|---|---|---|---|---|---|
| appetite | | | | | |
| Absence of well-being | 8.3 | 4.1 | 6.5 | 7.8 | 5.9 |
| Dyspnoea | 6.8 | 2.5 | 5.2 | 6.3 | 4.8 |
| Quality of life | 7.5 | 2.5 | 7.0 | 7.0 | 5.0 |

As demonstrated by these data, the composition described in example 1 has a marked effect on vitality in general, on peripheral pain, which significantly influences the mood, and on the appetite, probably due to an acceleration of gastric voiding and a reduction in the feeling of nausea or improved liver function. A direct comparison between the treatment with the composition described in example 1 and other treatments shows that the average score obtained restores the quality of the life of this group of patients to a normal state (score 0-3), while the placebo group remains in a pathological condition (score 6-7) and the other groups in a subclinical state (score 5-6), despite the expected improvement in some parameters. The major, unexpected improvement in the quality of life activates a favourable process, increasing the desire for protein-based foods, probably associated with liver reactivation and improved intestinal transit, probably due to a choleretic effect of the silybin complex with phospholipids. The intake of protein-based foods, with reinstatement of the muscle masses and physical activities, reverses the catabolic trend, alleviating the sensation of fatigue and, as demonstrated by some studies, significantly contributing to the patient's psychosocial recovery.

The invention claimed is:

1. A pharmaceutical composition for treating cancer-related fatigue comprising effective amounts of the following active ingredients:

(a) a *Panax ginseng* CA Mayer extract, (b) a *Zingiber officinale* extract, (c) an *Echinacea angustifolia* extract, and (d) silybin complexed with phospholipids, wherein the active ingredients are in admixture with one or more pharmaceutically-acceptable excipients, and wherein said pharmaceutical composition is in a form selected from the group consisting of a tablet, a pill, and a capsule.

2. The composition according to claim 1 wherein the extracts of *Zingiber officinale* and *Echinacea angustifolia* are lipophilic extracts.

3. The pharmaceutical composition according to claim 1 wherein the *ginseng* extract has a ginsenoside content of 8% with a ginsenoside Rg1/ginsenoside Rb1 ratio of 0.5/1, the *Zingiber officinale* extract has a gingerol content of 30% and the *Echinacea angustifolia* extract has an isobutylamide content higher than 20% by weight.

4. The pharmaceutical composition according to claim 1, wherein the pill is a sugar-coated pill, and wherein the capsule is selected from the group consisting of a soft-gelatin capsule, a hard-gelatin capsule, and a cellulose capsule.

5. A method of treating cancer-related fatigue in a patient in need thereof comprising administering an effective amount of the pharmaceutical composition of claim 1 to said patient.

* * * * *